United States Patent [19]
Alfano et al.

[11] Patent Number: 5,813,988
[45] Date of Patent: Sep. 29, 1998

[54] TIME-RESOLVED DIFFUSION TOMOGRAPHIC IMAGING IN HIGHLY SCATTERING TURBID MEDIA

[75] Inventors: Robert R. Alfano; Wei Cai; Feng Liu, all of Bronx, N.Y.; Melvin Lax, Summit, N.J.; Bidyut B. Das, Flushing, N.Y.

[73] Assignee: Research Foundation, New York, N.Y.

[21] Appl. No.: 618,471

[22] Filed: Mar. 18, 1996

Related U.S. Application Data

[63] Continuation-in-part of Ser. No. 384,112, Feb. 3, 1995, Pat. No. 5,625,458.
[51] Int. Cl.$^6$ ........................................................ A61B 5/00
[52] U.S. Cl. .......................... 600/476; 600/473; 356/432; 356/446
[58] Field of Search ...................................... 128/664, 665, 128/633; 356/446, 237, 239, 240, 432, 436, 441; 250/341.1, 358.1; 600/310, 473, 476

[56] References Cited

U.S. PATENT DOCUMENTS

| | | |
|---|---|---|
| 5,213,105 | 5/1993 | Gratton et al. . |
| 5,353,799 | 10/1994 | Chance . |
| 5,371,368 | 12/1994 | Alfano et al. .......................... 250/341.1 |
| 5,416,582 | 5/1995 | Knutson et al. . |
| 5,441,054 | 8/1995 | Tsuchiya . |
| 5,555,885 | 9/1996 | Chance . |
| 5,596,987 | 1/1997 | Chance . |
| 5,644,429 | 7/1997 | Alfano et al. ............................ 359/559 |

OTHER PUBLICATIONS

Alfano et al. "Photons for Prompt Tumour Detection", Physics World, pp. 37–40, Jan. 1992.
Wang et al., "Ballistic 2–D Imaging Through Scattering Walls Using an Ultrafast Optical Kerr Gate," Science, 253:769–71 (1991).
Das et al., "Ultrafast time–gated imaging in thick tissues: a step toward optical mammography," Opt. Lett., 18:1092–4 (1993).
Alfano et al., "Time–Resolved Imaging of Translucent Droplets in Highly Scattering Turbid Media," Science, 264:1913–5 (1994).

(List continued on next page.)

*Primary Examiner*—Marvin M. Lateef
*Assistant Examiner*—Shawna J. Shaw
*Attorney, Agent, or Firm*—Kriegsman & Kriegsman

[57] ABSTRACT

A method for imaging objects in highly scattering turbid media. According to one embodiment of the invention, the method involves using a plurality of intersecting source/detectors sets and time-resolving equipment to generate a plurality of time-resolved intensity curves for the diffusive component of light emergent from the medium. For each of the curves, the intensities at a plurality of times are then inputted into the following inverse reconstruction algorithm to form an image of the medium:

$$X^{(k+1)^T} = [Y^T W + X^{(k)^T} \Lambda ][W^T W + \Lambda]^{-1}$$

wherein W is a matrix relating output at detector position $r_d$, at time t, to source at position $r_s$, $\Lambda$ is a regularization matrix, chosen for convenience to be diagonal, but selected in a way related to the ratio of the noise, <nn> to fluctuations in the absorption (or diffusion) $X_j$ that we are trying to determine:

$$\Lambda_{ij} = \lambda_j \delta_{ij} \text{ with } \lambda_j = <nn>/<\Delta Xj \Delta Xj>$$

Here Y is the data collected at the detectors, and $X^k$ is the kth iterate toward the desired absoption information.

26 Claims, 11 Drawing Sheets

OTHER PUBLICATIONS

Huang et al., "Optical Coherence Tomography," Science, 254:1178–81 (1991).

Chance et al., "Highly sensitive object location in tissue models with linear in–phase and anti–phase multi–element optical arrays in one and two dimensions," Proc. Natl. Acad. Sci. USA, 90:3423–7 (1993).

Fishkin et al., "Propagation of photon–density waves in strongly scattering media containing an absorbing semi–infinite plane bounded by a straight edge," J. Opt. Soc. Am. A, 10(1):127–40 (1993).

Singer et al., "Image Reconstruction of the Interior of Bodies That Diffuse Radiation," Science, 248:990–3 (1990).

Arridge, "The Forward and Inverse Problems in Time Resolved Infra–red Imaging," Medical optical tomography: functional imaging and monitoring, SPIE Institutes, vol. IS11, G. Muller ed., pp. 31–64 (1993).

Barbour et al., "A Perturbation Approach for Optical Diffusion Tomography Using Continuous–Wave and Time–Resolved Data," Medical optical tomography: functional imaging and monitoring, SPIE Institutes, vol. IS11, G. Muller ed., pp. 87–120 (1993).

Shaw, Jr., "Improvement of the Resolution of an Instrument by Numerical Solution of an Integral Equation," J. Math. Analys. and Applic., 37:83–112 (1972).

Without iteration, Running time: 1 minute on SGI Indy computer.

*FIG. 5(a)*

Iteration m=2000, Running time: 3 hours on SGI Indy computer.

TIME-RESOLVED DIFFUSION TOMOGRAPHIC IMAGING IN HIGHLY SCATTERING TURBID MEDIA

CROSS-REFERENCE TO RELATED APPLICATIONS

The present application is a continuation-in-part of presently pending U.S. patent application Ser. No. 08/384,112, filed Feb. 3, 1995, now U.S. Pat. No. 5,625,458 issued Apr. 29, 1997, which is incorporated herein by reference.

STATEMENT AS TO RIGHTS TO INVENTIONS MADE UNDER FEDERALLY-SPONSORED RESEARCH AND DEVELOPMENT

This invention was made, in part, with Government support awarded by NASA and ONR. The Government may have certain rights in this invention.

BACKGROUND OF THE INVENTION

The present invention relates generally to the imaging of objects in highly scattering turbid media and more particularly to a novel technique for imaging objects in highly scattering turbid media.

As can readily be appreciated, there are many situations in which the detection of an object present in a highly scattering turbid medium is highly desirable. For instance, the detection of a tumor embedded within a tissue is one such example. Although X-ray techniques do provide some measure of success in detecting objects in turbid media, they are not well-suited for detecting very small objects, e.g., tumors less than 1 mm in size, or for detecting objects in thick media. In addition, X-ray radiation can present safety hazards to a person exposed thereto.

An alternative technique used to detect objects in turbid media is transillumination. In transillumination, visible or near infrared (NIR) light is incident on one side of a medium and the light emergent from the opposite side of the medium is used to form an image. Objects embedded in the medium typically absorb the incident light and appear in the image as shadows. Unfortunately, the usefulness of transillumination as a detection technique is severely limited in those instances in which the medium is thick or the object is very small. This is because light scattering within the medium contributes to noise and reduces the intensity of the unscattered light used to form the image shadow.

To improve the detectability of small objects located in a turbid medium using transillumination, many investigators have attempted to selectively use only certain components of the transilluminating light signal. This may be done by exploiting the properties of photon migration through a scattering medium. Photons migrating through a turbid medium have traditionally been categorized into three major signal components: (1) the ballistic (coherent) photons which arrive first by traveling over the shortest, most direct path; (2) the snake (quasi-coherent) photons which arrive within the first δt after the ballistic photons and which deviate, only to a very slight extent, off a straight-line propagation path; and (3) the diffusive (incoherent) photons which experience comparatively more scattering than do ballistic and snake photons and, therefore, deviate more considerably from the straight-line propagation path followed by ballistic and snake photons.

Because it has been believed that ballistic and snake photons contain the least distorted image information and that diffusive photons lose most of the image information, efforts to make transillumination work most effectively with turbid media have focused on techniques which permit the selective detection of ballistic and snake photons while rejecting diffusive photons. This process of selection and rejection has been implemented in various time-gating, space-gating and time/space-gating techniques. Patents, patent applications and publications which disclose certain of these techniques include U.S. Pat. No. 5,140,463, inventors Yoo et al., which issued Aug. 18, 1992; U.S. Pat. No. 5,143,372, inventors Alfano et al., which issued Aug. 25, 1992; U.S. Pat. No. 5,227,912, inventors Ho et al., which issued Jul. 13, 1993; U.S. Pat. No. 5,371,368, inventors Alfano et al., issued Dec. 6, 1994; Alfano et al., "Photons for prompt tumor detection," *Physics World*, pp. 37–40 (January 1992); Wang et al., "Ballistic 2-D Imaging Through Scattering Walls Using an Ultrafast Optical Kerr Gate," *Science*, Vol. 253, pp. 769–771 (Aug. 16, 1991); Wang et al., "Kerr-Fourier imaging of hidden objects in thick turbid media," *Optics Letters*, Vol. 18, No. 3, pp. 241–243 (Feb. 1, 1993); Yoo et al., "Time-resolved coherent and incoherent components of forward light scattering in random media," *Optics Letters*, Vol. 15, No. 6, pp. 320–322 (Mar. 15, 1990); Das et al., "Ultrafast time-gated imaging in thick tissues: a step toward optical mammography," *Optics Letters*, 18(13):1092–4 (1993); Chen et al., "Two-dimensional imaging through diffusing media using 150-fs gated electronic holography techniques," *Optics Letters*, Vol. 16, No. 7, pp. 487–489 (Apr. 1, 1991); Duncan et al., "Time-gated imaging through scattering media using stimulated Raman amplification," *Optics Letters*, Vol. 16, No. 23, pp. 1868–1870 (Dec. 1, 1991), all of which are incorporated herein by reference.

Of the above-listed art, Wang et al., "Kerr-Fourier imaging of hidden objects in thick turbid media," *Optics Letters*, Vol. 18, No. 3, pp. 241–243 (Feb. 1, 1993) is illustrative of transillumination techniques which selectively use the ballistic and/or snake components of light. In this article, there is disclosed a time/space-gating system for use in imaging opaque test bars hidden inside a 5.5 cm-thick 2.5% Intralipid solution. The disclosed system includes three main parts: a laser source, an optical Kerr gate and a detector. The laser source is a picosecond mode-locked laser system, which emits a 1054 nm, 8 ps laser pulse train as the illumination source. The second harmonic of the pulse train, which is generated by transmission through a potassium dihydrate phosphate (KDP) crystal, is used as the gating source. The illumination source is sent through a variable time-delay and is then used to transilluminate, from one side, the turbid medium containing the opaque object. The signal from the turbid medium located at the front focal plane of a lens is collected and transformed to a Kerr cell located at its back focal plane (i.e., the Fourier-transform spectral plane of a 4F system). That portion of the Kerr cell located at the focal point of the 4F system is gated at the appropriate time using the gating source so that only the ballistic and snake components are permitted to pass therethrough. The spatial-filtered and temporal-segmented signal is then imaged by a second lens onto a CCD camera.

Although techniques of the type described above, which selectively use ballistic and snake photons to image objects in turbid media, have enjoyed a modicum of success, such techniques have been limited by the fact that detected light signals derived from ballistic and snake photons are typically rather weak, due to the proportionately small number of transilluminated ballistic and snake photons. This problem is further exacerbated in those instances in which the turbid medium is thick and the likelihood of substantial scattering increases.

Accordingly, because diffusive photons constitute the greatest component of the transilluminated light signal, it would be highly desirable to make use of the diffusive component of the light signal in forming an image via transillumination. This objective is made difficult, however, by the fact that diffusive photons tend to traverse a medium along ill-defined paths. One approach to this problem has been to invert the experimental scattering data obtained from various points in the medium using some inverse algorithm and reconstruction approach. This approach is often called diffusion tomography since diffusion or scattering is the dominant factor in the problem. In diffusion tomography, one produces an internal map of the scattering medium using the scattered signals and a mathematical inversion algorithm. The inversion is based upon the physical and mathematical principles governing photon propagation in turbid media. Both time-resolved data and frequency domain data can be used for reconstruction. Examples of diffusion tomography techniques include Arridge, "The Forward and Inverse Problems in Time Resolved Infra-Red Imaging," *Medical Optical Tomography: Functional Imaging and Monitoring SPIE Institutes,* Vol. IS11, G. Muller ed., 31–64 (1993); Singer et al., "Image Reconstruction of the Interior of Bodies That Diffuse Radiation," *Science,* 248:990–3 (1993); Barbour et al., "A Perturbation Approach for Optical Diffusion Tomography Using Continuous-Wave and Time-Resolved Data," *Medical Optical Tomography: Functional Imaging and Monitoring SPIE Institutes,* Vol. IS11, G. Muller ed., 87–120 (1993); M. Patterson et al., *SPIE,* 1767, 372 (1992); J. Schotland et al., *App. Opt.,* 32, 448 (1993), all of which are incorporated herein by reference.

The foregoing diffusion tomography techniques do not lead to a resolution that is better than about 5–10 mm. Moreover, these techniques are time-consuming and do not readily lend themselves to real-time use.

SUMMARY OF THE INVENTION

It is an object of the present invention to provide a novel technique for imaging objects present in highly scattering turbid media.

It is another object of the present invention to provide a technique as described above that overcomes at least some of the disadvantages associated with existing techniques for imaging objects in highly scattering turbid media.

Additional objects, as well as features and advantages, of the present invention will be set forth in part in the description which follows, and in part will be obvious from the description or may be learned by practice of the invention.

The present invention is based on the present inventors' discovery that objects hidden in highly scattering turbid media can be imaged by a novel, fast and noise-resistant inverse method which involves illuminating a highly scattering turbid medium with a pulse of light, the light emergent from the highly scattering turbid medium consisting of a ballistic component, a snake-like component and a diffusive component; determining the intensity of said diffusive component at a plurality of points in time; and using said intensity determinations to form an image of the object in the highly scattering turbid medium.

The aforementioned illuminating and determining steps preferably include the use of a light source and one or more detectors, said detectors preferably including means, such as a streak camera, for temporally resolving the diffusive component of the emergent light from the highly scattering turbid medium. More preferably, two or more source/detector sets are arranged in an intersecting manner to enable a 2-D or 3-D image to be formed.

Preferably, the following inverse reconstruction algorithm is used to form an image of the turbid medium using the aforementioned intensity determinations:

$$X^{(k+1)^T} = [Y^T W + X^{(k)^T} \Lambda ][W^T W + \Lambda]^{-1}$$

wherein W is a matrix relating output at detector position $r_d$, at time t, to source at position $r_s$, $\Lambda$ is a regularization matrix, chosen for convenience to be diagonal, but selected in a way related to the ratio of the noise, $<nn>$ to fluctuations in the absorption (or diffusion) $X_j$ that we are trying to determine:

$$\Lambda_{ij} = \lambda_j \delta_{ij} \text{ with } \lambda_j = <nn>/<\Delta Xj \Delta Xj>$$

Here Y is the data collected at the detectors, and $X^k$ is the kth iterate toward the desired absoption information.

A distinct advantage of the present method, over existing inverse reconstruction methods for imaging objects located in highly scattering turbid media using diffusive photons, is that the present method can be done with fewer iterations, thereby making possible real-time imaging.

The present invention is also directed to systems constructed in accordance with the foregoing methods.

In the description which follows, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

As indicated above, the present invention is based upon the present inventors' discovery that objects hidden in highly scattering turbid media can be imaged by a novel, fast and noise-resistant inverse method which comprises, among other things, transilluminating a highly scattering turbid medium using a plurality of intersecting source-detector pairs and using intensity measurements of the diffusive component of the detected light signals taken over a plurality of time windows (or "time-slices") in a novel inverse reconstruction algorithm.

The following discussion provides the theoretical basis for the present invention: A scattered signal is, in general, a function of key parameters characterizing the medium. The forward problem is to build a mathematical model that allows computation of signals when a spatial distribution of key parameters is given. This mathematical model is clearly based on the fundamental physical principles governing the interaction. The inverse problem is to find the distribution of these key parameters that best fit the given signal data. For photon propagation in turbid media, the key parameters characterizing the interaction are the absorption length, the transport mean free path, the scattering mean free path, and the index of refraction of media. The parameters are in general functions of position $(\vec{r})$ and wavelength $(\lambda)$. In the case of optical diffusion tomography, the most commonly used key parameters are absorption and transport scattering coefficients, which are the inverse of absorption length and transport scattering mean free path, respectively. The mathematical model governing the photon propagation is the photonic transport theory or its approximations, such as the diffusion theory or the telegrapher's equation.

To show the basic principle of this technique, diffusion theory is applied here to model light propagation in turbid media. The diffusion equation in turbid media is $$\left[ \frac{\partial}{\partial t} + c\mu_a(\vec{r}) - \nabla(cD(\vec{r})\nabla) \right] I(\vec{r},t) = S(\vec{r},t) \tag{1}$$

where $I(\vec{r},t)$ is the field of photon density, $S(\vec{r},t)$ is the source of laser light, $\mu_a$ is the absorption coefficient, $D=1/[3(\mu_a+(1-g)\mu_s)]$ is the diffusion coefficient, with $\mu_s$ the scattering coefficient, g the scattering anisotropic factor and c the speed of light in the medium.

We are interested in the following problem: given intensity measurements taken around the media either with objects located therein, $I(\vec{r},t)$, or without objects located therein, $I_0(\vec{r},t)$, reconstruct a spatial map of the change in optical parameters (absorption and diffusion coefficients) due to the presence of hidden objects.

The forward problem of scattering can be represented in a matrix form written as $$Y = WX + n \tag{2}$$

where Y has M=(number of S-D pairs)×(number of time slices) elements, which is the change in intensity profile and is a function of the position of source $\vec{r}_s$, the position of detector $\vec{r}_d$, and the time-slice in the profile t. X has N=(number of voxel) elements wherein a voxel is a space grid element. $X_j = c\Delta\mu_a(\vec{r}_j)$ or $c\Delta D(\vec{r}_j)$ is the (time-independent) change in the absorption coefficient or the diffusion coefficient in the voxel j due to the presence of hidden objects, and n is signal detector noise. W is an M×N matrix. Its element is the weight function or "photon measurement density functions." This weight function represents the change in signal at the detector placed at $\vec{r}_d$ at time t from a source signal originating at $\vec{r}_s$ associated with a unit change in absorption coefficient (or diffusion coefficient) at $\vec{r}_j$ of the reference medium, as implemented by a diffusion process that carries the signal from source at $\vec{r}_s$ to the detector at $\vec{r}_d$. Its value is theoretically calculated according to the mathematical model, for example, the diffusion theory in the case shown below.

Using Green's function formula, for the case of absorption change, $c\Delta\mu_a$, the element of W is given by $$W[\vec{r}_d,\vec{r}_s,t),\vec{r}_j] = \frac{\Delta V}{G^0(\vec{r}_d,\vec{r}_s,t)} \int_0^t d\tau G^0(\vec{r}_d,\vec{r}_j,t-\tau)G^0(\vec{r}_j,\vec{r}_s,\tau) \tag{3}$$

where $G^0(\vec{r}_j,\vec{r}_i,t)$ is the Green's function of Eq.(1) for a reference system (the system with no hidden object) which gives the normalized photon intensity at $\vec{r}_j$ at time t as migrating photons originate from $\vec{r}_i$ at time t=0. In Eq.(3), the second Green's function in the integral, $G^0(\vec{r}_j,\vec{r}_s,\tau)$ represents the photons that migrate from a source to a given voxel element. The first one, $G^0(\vec{r}_d,\vec{r}_j,t-\tau)$, represents the photons that migrate from this voxel to a detector. $\Delta V$ is volume of a voxel. Therefore, W in Eq.(3) represents a normalized effect that photons originating from the source migrate through voxel j, then further migrate to the detector during a total time of t. In the case of diffusion or scattering change, both $G^0$ in the integral of Eq.(3) are replaced by $\nabla G^0$.

According to certain previously-used inversion algorithms employed in image reconstruction, such as Algebraic Reconstruction Technique (ART), Simultaneous Algebraic Reconstruction Technique (SART) or Conjugate Gradients (CGD), the fractional signal change $Y=-(I-I_0)/I_0$, which corresponds to the first order perturbation, is used. Such inversion reconstruction algorithms, however, generally requires a great number of iterations in order for a clear image map of hidden objects to be obtained. Such iterations frequently can take an amount of calculation time that exceeds the practical time limit for clinical applications.

A more accurate non-perturbative approximation based on a cumulant expansion has been developed by us, which fits the experimental data by $Y=-\ln(I/I_0)$. This treatment, to some extent, automatically includes higher order non-linear contributions. The inversion is a reconstruction of optical parameters from signals. In order to make a fast inversion for clinical applications, we have developed the following novel inverse reconstruction procedure based on a modification of the iteration formula described in Shaw, "Improvement of the Numerical Resolution of An Instrument by Numerical Solution of the Integral Equation," *J. Math. Analys. and Applic.*, 37:83–112 (1972), which is incorporated herein by reference:

$$X^{(k+1)T} = [Y^T W + X^{(k)T} \Lambda][W^T W + \Lambda]^{-1}$$

where Y, $(-\ln(I/I_0))$, is the input data for inversion. $X^{(k)}$ and $X^{(k+1)}$ are $k^{th}$ and $(k+1)^{th}$ iteration solutions, respectively, for the change of parameters. The initial value of X is set to zero in the absence of prior information about hidden objects. T represents the transpose matrix. The matrix $\Lambda$, which regularizes or converts an ill-posed problem to a well-posed problem, is chosen to be diagonal, $\Lambda_{ij}=\lambda_j\delta_{ij}$. $\lambda_j = <nn>/$ $<\Delta X_j \Delta X_j>$, with $< \ldots >$ the statistical average, and $\Delta X_j = X_j - <X_j>$. Thus, $\lambda_j$ represents the ratio of mean square of noise to the expected mean square deviation in the change of parameters (structural noise).

Since W does not relate to the position and optical parameters of hidden objects, having W for a given reference system (either homogeneous or inhomogeneous), the inverse matrix $[W^T W + \Lambda]^{-1}$ can be precalculated and stored as a database, which can be used in clinical cases to find hidden objects. This strategy separates time-consuming work in inversion processes into two parts. Pre-computation is time-consuming and may require the use of a supercomputer. However, it greatly reduces the burden of performing inverse processes in daily clinical cases.

One of the main difficulties in inversion is that most of inverse problems are ill-posed. If no noise would exist, an inverse image can be reconstructed from Eq.(2) via: $X^T = Y^T W [W^T W]^{-1}$. Existence of small noises should not have much effect on results obtained. However, the matrix $W^T W$ is generally ill-posed or near-singular, namely, this matrix has some near-zero eigen values. This occurs when the number of measurements M is less than the number of unknown parameters N, or the measured signals are not fully independent of each other. In this case, the effect of small noise will be magnified in the inverse process, and the solution of inversion becomes unstable. One of the methods to overcome the ill-posed problems is regularization, that adds a $\Lambda$ to the matrix $W^T W$. $\Lambda$ is relatively small compared to the matrix $W^T W$; therefore, regularization makes the matrix well-posed or well defined, but does not change the characteristics of the image map. The value of $\Lambda$ is set according to the experimental noise level and structural noise present in the change of optical parameters. If $\|\Lambda W^T W\| < 1$, one may use the following expansion to correct error introduced by regularization:

$$[W^T W]^{-1} = [B - \Lambda]^{-1} = B^{-1} + B^{-1} \Lambda B^{-1} + B^{-1} \Lambda B^{-1} \Lambda B^{-1} + \ldots \quad (5)$$

The iterations in Eq.(4) are equivalent to the above expansion.

If noise n exists, $Y = WX + n$. One wants to find an inverse operator, $\hat{X} = \hat{L}Y$, which gives the estimated value $\hat{X}$ of X, that, in the sense of statistical average, has minimum error. Shaw has derived the following solution:

$$\hat{X} = [Y^T W < \Delta X \Delta X > + <X><nn>] \times [<\Delta X \Delta X> W^T W + <nn>]^{-1} \quad (6)$$

with $< \ldots >$ statistical average, $\Delta X = X - <X>$. We see that Eq.(6) is a well-posed expression. This approach is the so-called "well-posed stochastic extension of ill-posed linear processes" or "statistical regularization." Comparing Eq.(4) and Eq.(6), $\Lambda$ in Eq.(4) is related to $<nn>/<\Delta X \Delta X>$. Thus, $\lambda_j$ represents the ratio of mean square of detector noise to the expected mean square deviation in the change of parameters (structural noise).

The key point is that since W is only reference related, and does not relate to the position and optical parameters of hidden objects, the inverse matrix $[W^T W + \Lambda]^{-1}$ of a given pattern of the reference system, which can be either homogenous or inhomogeneous, can be pre-calculated and pre-stored as a database for various patients for clinical use.

Our tests show that this novel inverse procedure converges after only 2–4 iterations, which is much faster than the ART or SART procedures currently used. It takes about one minute to form an image in our reconstruction tests on a Silicon Graphic Instruments (SGI) workstation computer.

Figure 1A:
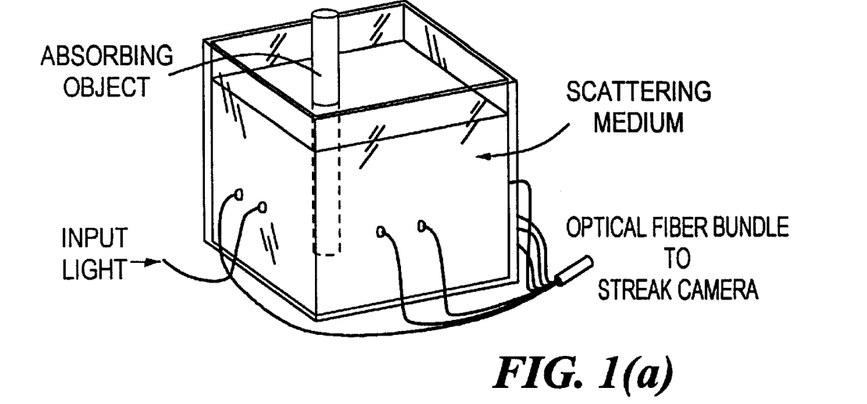
FIGS. 1(a) and 1(b) are views of an experimental setup used to test the imaging method of the present invention.
Figure 1B:
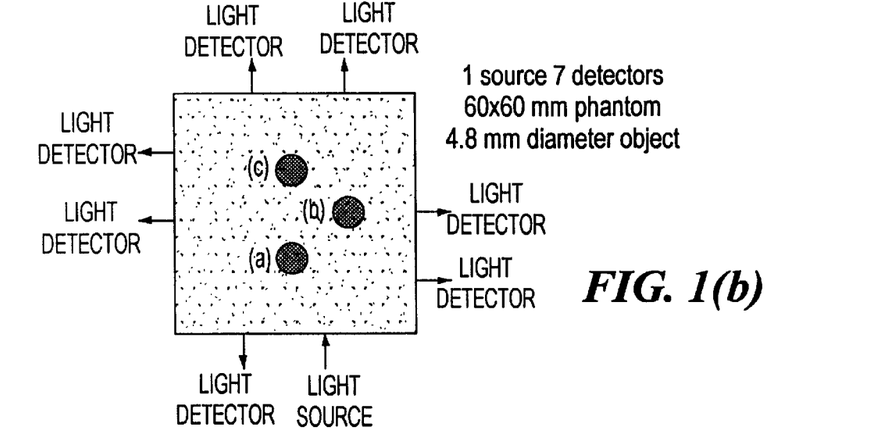

To demonstrate the present technique, the following experiment was performed. Schematic drawings of the experimental arrangement are shown in FIGS. 1(a) and 1(b). Ultrashort pulses of 100 fs pulse duration at a wavelength of 625 nm were coupled into a rectangular shape random medium by an optical fiber. This geometry was chosen because it is easy to construct an analytical expression of Green's function $G^0$ in a finite sized 3D volume, which is suitable for testing the physical modeling and the inversion algorithm. The scattered pulses around the medium were collected by 7 optical fibers and time resolved by a streak camera. The size of the sample was 60×60 mm and the height was 90 mm. The fibers were located at mid-plane. The source fiber was at the center of the boundary wall. Two fibers each were placed on the opposite and the side boundary walls of the sample, and one fiber detector was placed on the incident wall. The scattered pulses collected by the 7 detection fibers and a reference pulse were coupled onto the input slit of the streak camera for multi-channel detection. The medium was Intralipid solution with a transport mean free path of 2.5 mm and absorption length of about 500 mm. The hidden object was a black painted aluminum rod of diameter of 4.8 mm. Temporal profiles of the scattered pulses around the medium were measured. In this experimental setting, the structure was z-independent, so the reconstructed image is presented as a 2-D image. However, the present method is intrinsically a 3-D imaging model.

Figure 1C:
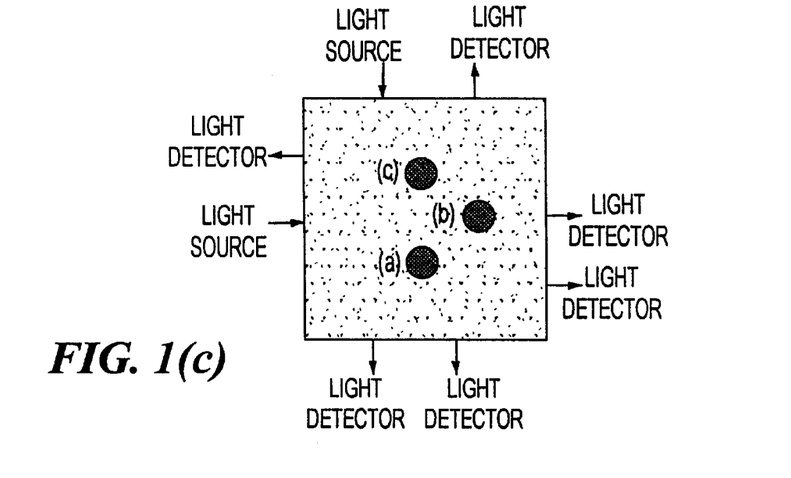
FIG. 1(c) is a top view of an alternative set-up to that of FIG. 1(b) wherein a pair of intersecting light source/detector sets are employed.

FIG. 1(c) shows a top view of an alternative set-up to that of FIG. 1(b) wherein a pair of intersecting light source/ detector sets are employed. The type of light source and the type of light detector used in FIG. 1(c) may be the same as that of FIG. 1(b).

Figure 2:
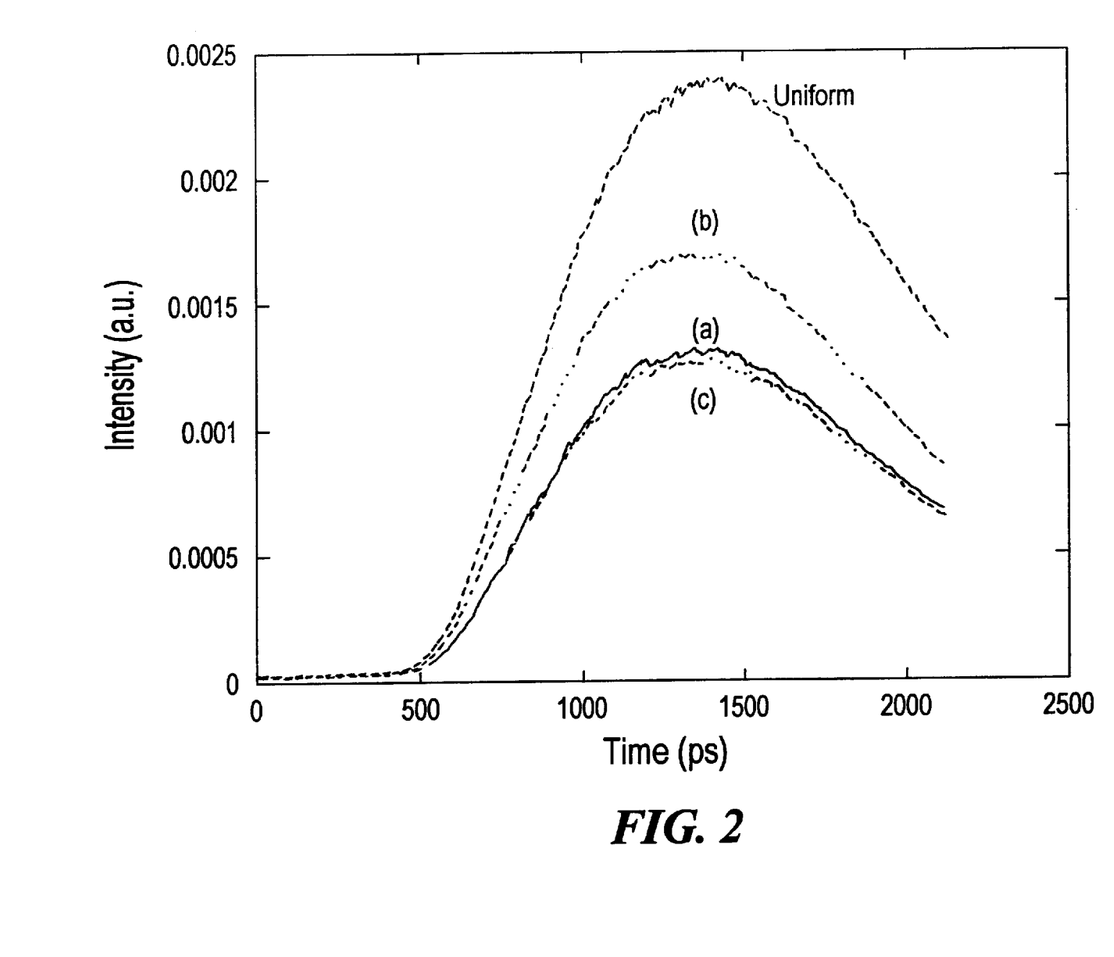
FIG. 2 is a graphic representation of various time-resolved curves obtained using the experimental setup of FIGS. 1(a) and 1(b), curves (a) through (c) being obtained by positioning an object in the three locations (a), (b) and (c), respectively, of FIG. 1(b), and the curve labelled "Uniform" being obtained by not positioning the object within the sample medium.
Figure 3A:
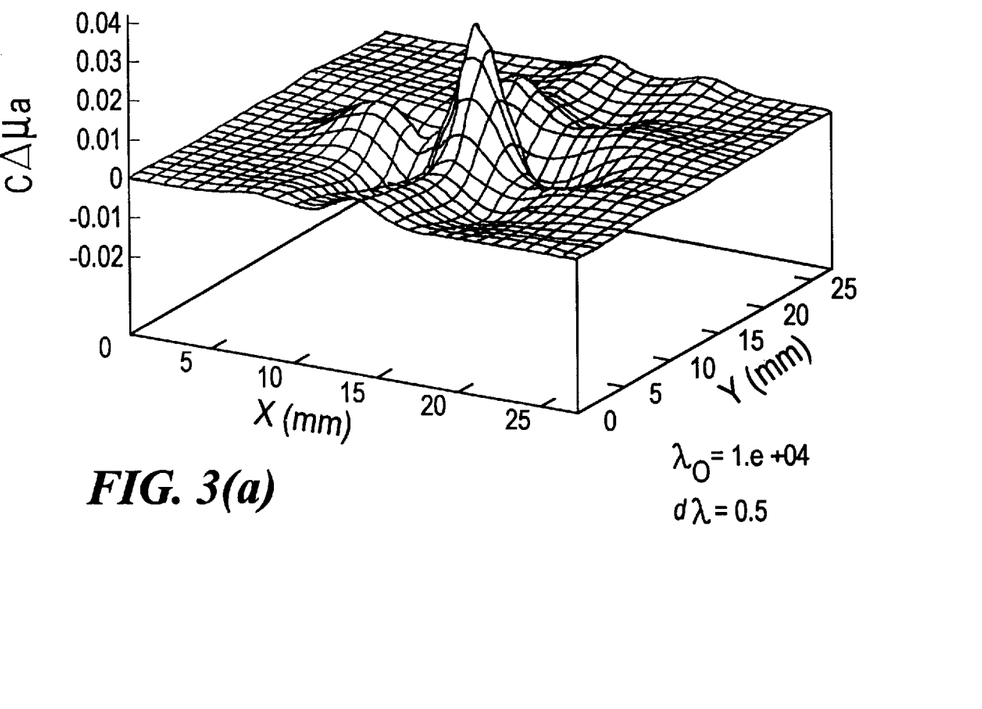
FIGS. 3(a) through 3(e) are comparative images of the object of FIG. 1(a) obtained using the method of the present invention with different regularization parameters.
Figure 3B:
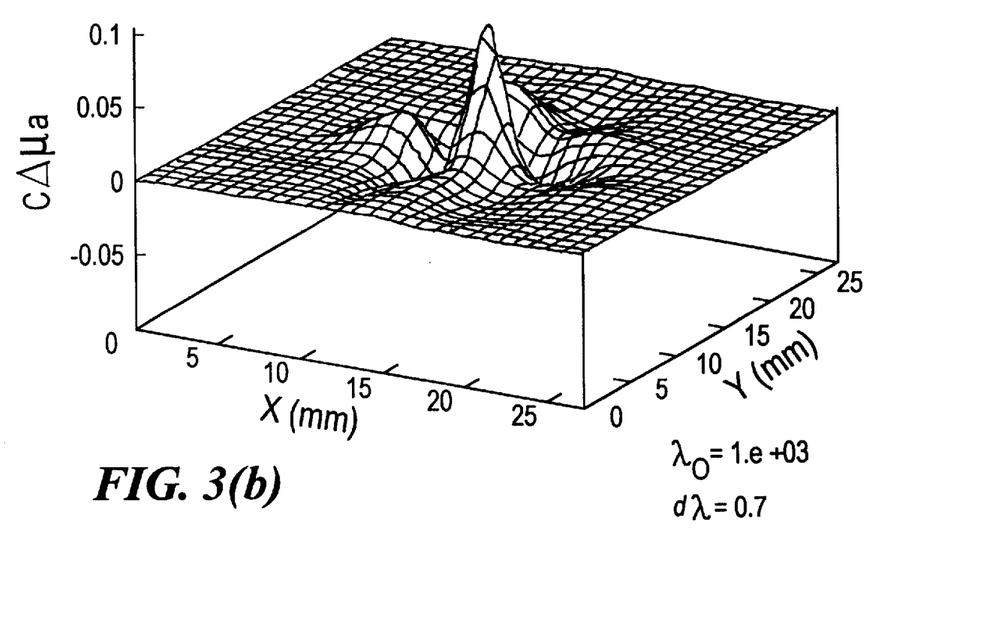
Figure 3C:
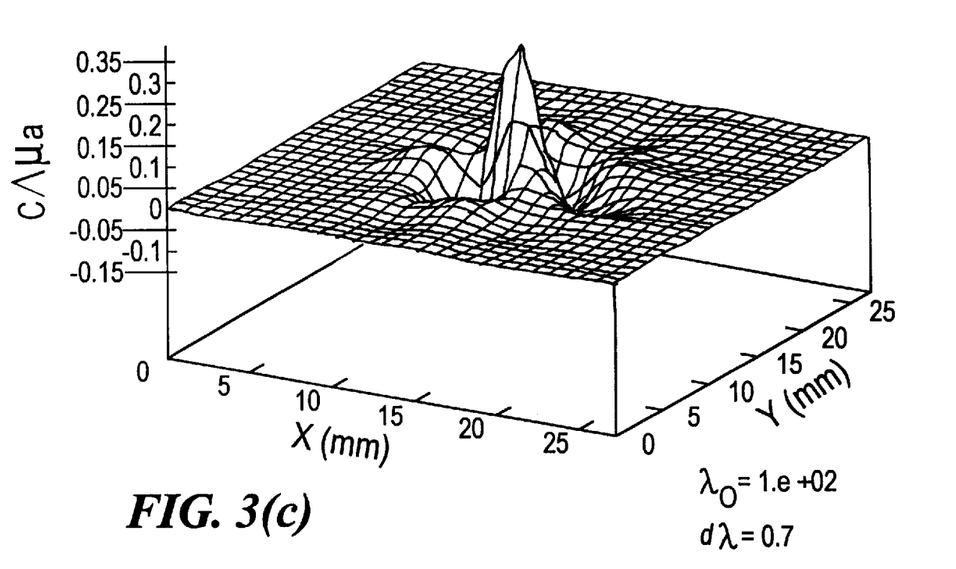
Figure 3D:
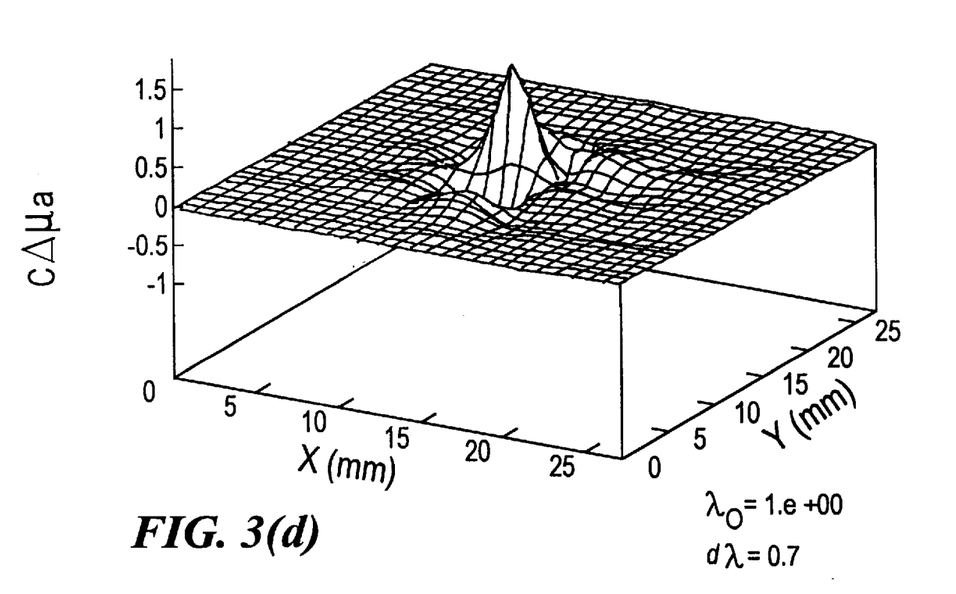
Figure 3E:
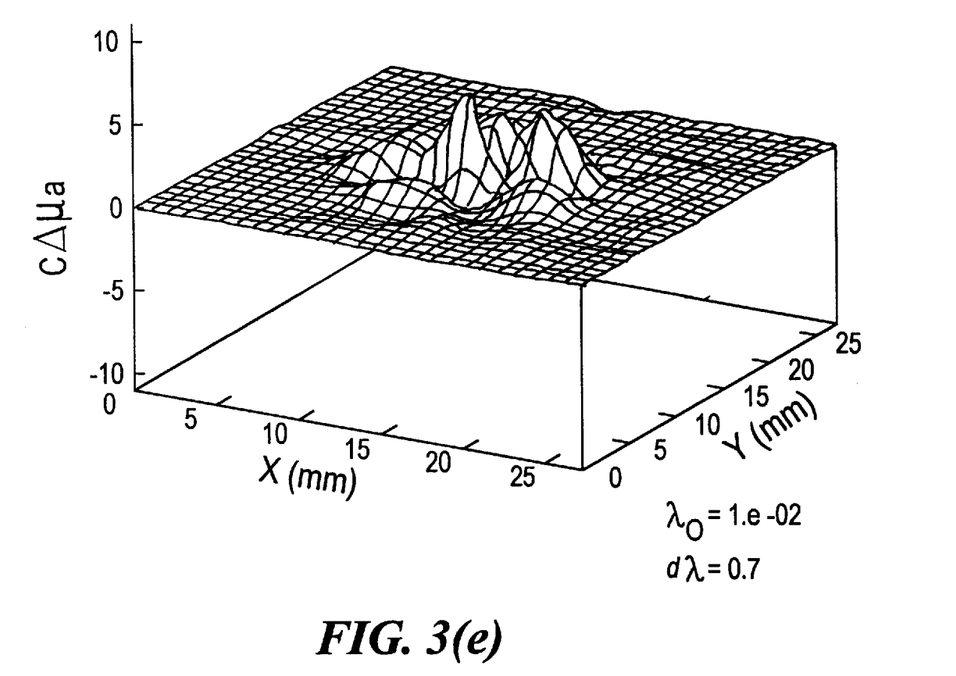
Figure 4A:
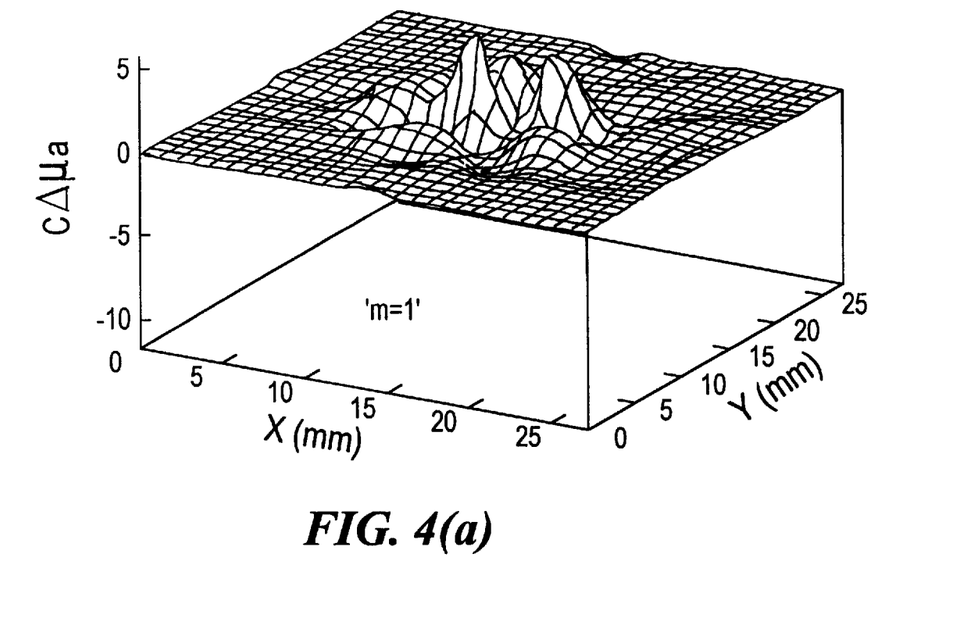
FIGS. 4(a) through 4(h) are comparative images of the object of FIG. 1(a) obtained using the method of the present invention with different numbers of iterations.
Figure 4B:
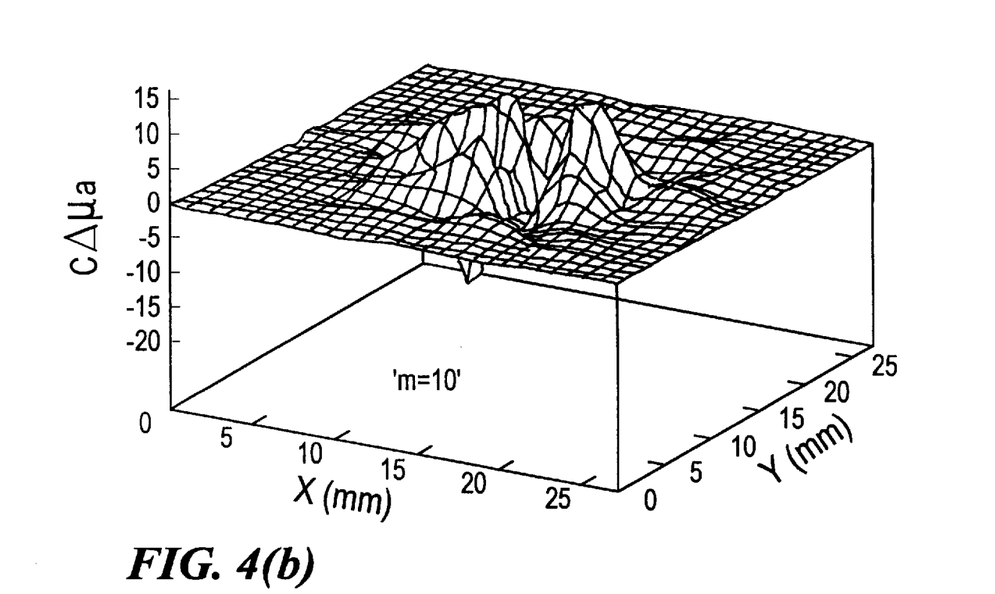
Figure 4C:
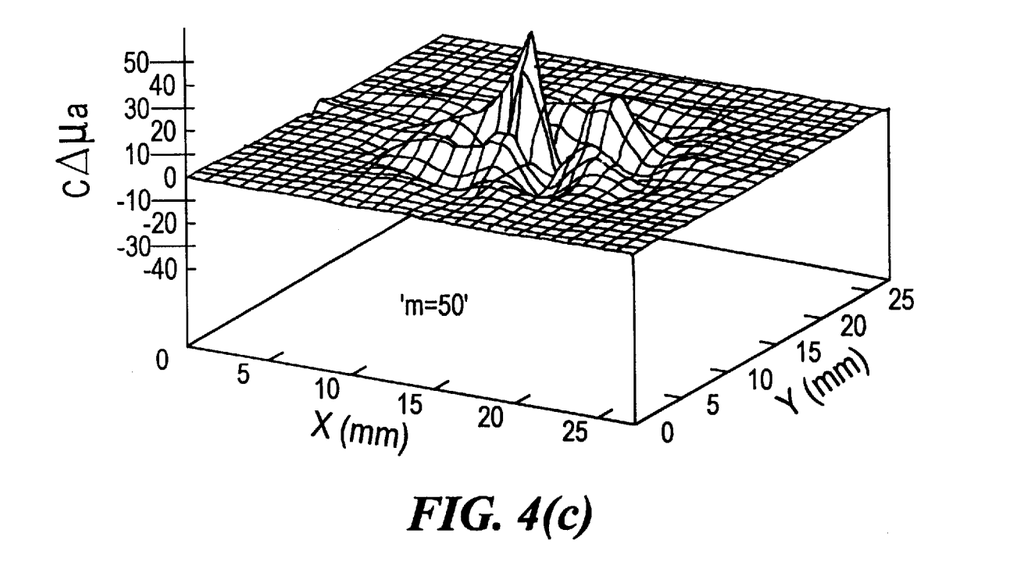
Figure 4D:
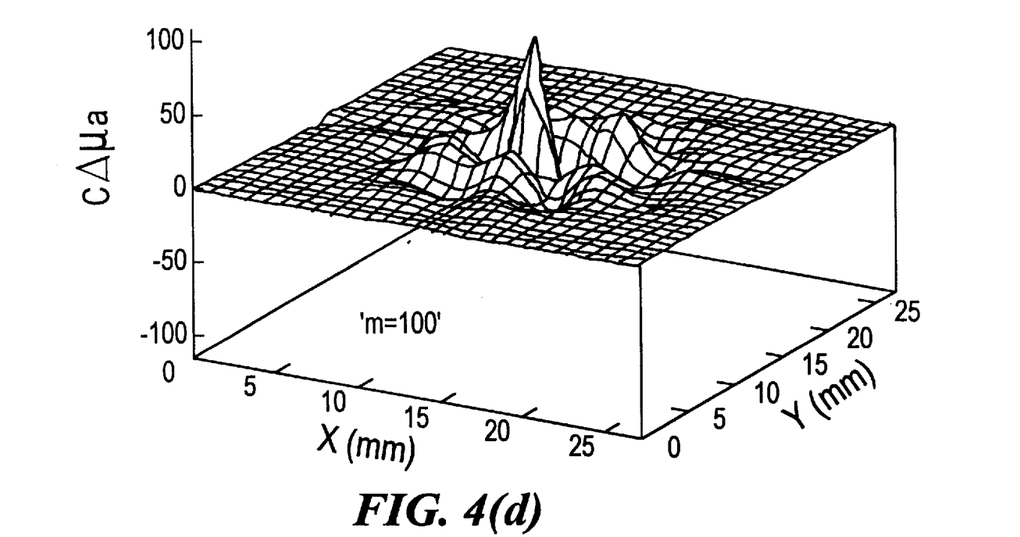
Figure 4E:
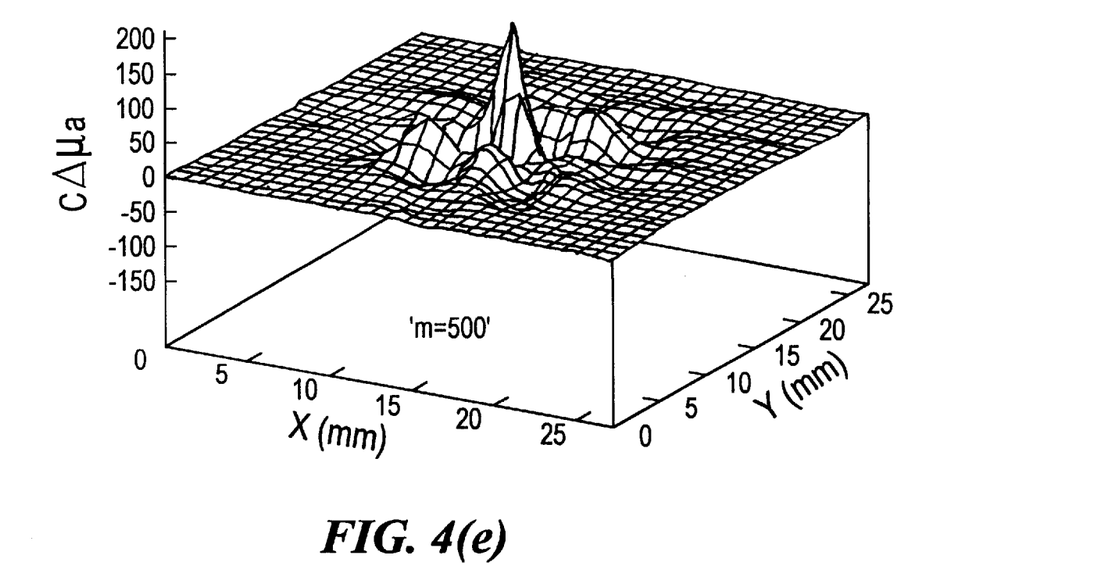
Figure 4F:
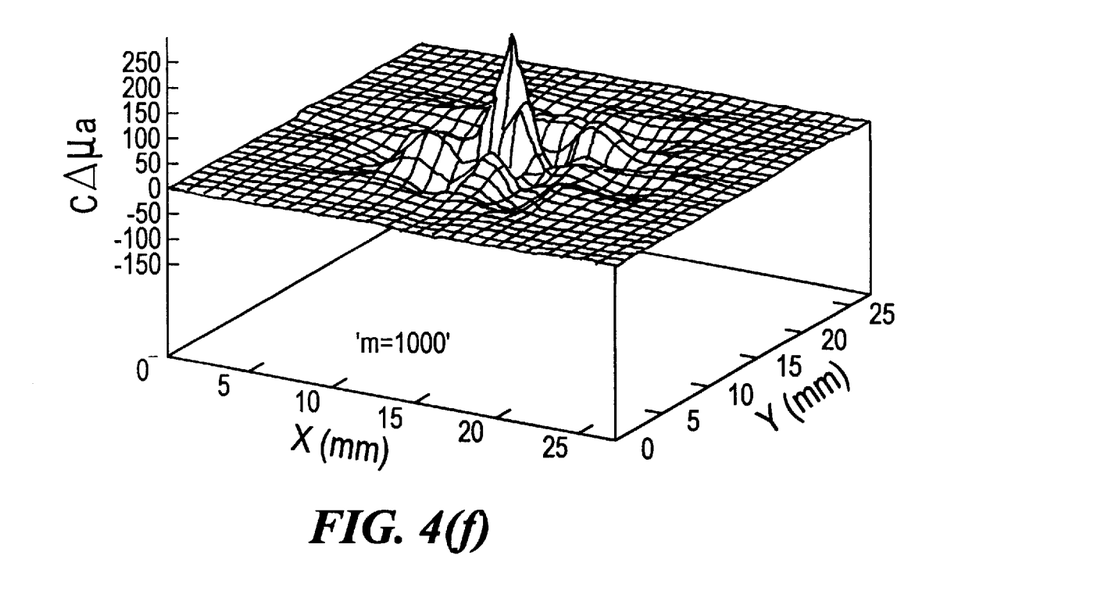
Figure 4G:
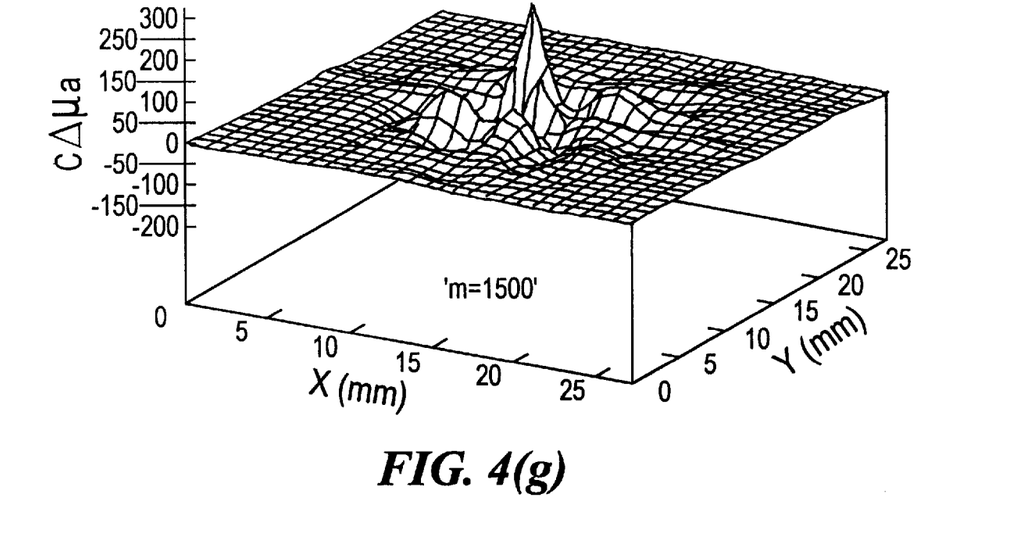
Figure 4H:
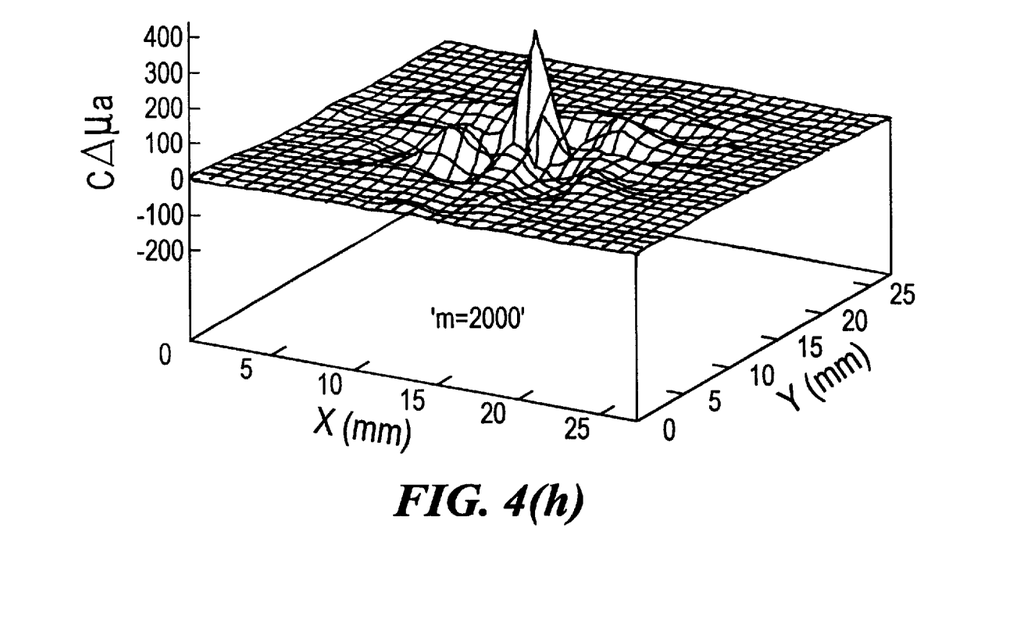

A typical set of temporal profiles measured for one S-D pair of FIG 1(b) is shown in FIG. 2. In this case, the detector is located straight across the medium in the line of incidence. Measurements of the uniform medium without the object and with the object placed in three locations 90 degrees apart are also shown. It is clearly shown that the intensity is reduced by introducing the absorbing object, and a larger reduction was observed when the object was placed in the line of the source detector pair. The measurement of 3 object positions is equivalent to 3 measurements by rotating the S-D pairs by 90 degrees while fixing the object location.

In the image reconstruction, an area in the sample was divided into 28×28=784 voxels which corresponds to an actual voxel size of 2×2 mm. Measurements of 7 S-D pairs with the above mentioned object locations were used. For each temporal intensity profile, intensity data at 40 time slices uniformly distributed from 602 ps to 2045 ps were used. Thus, the total number of input data points was 21×40=840. This is one of the important features of our method—the use of hundreds of time slices from the temporal profile of one S-D pair for image reconstruction gives much more information than data obtained in the frequency domain with much higher speed resolution in sub-mm to mm range to detect a defect. The robustness of the method was demonstrated with a small number of fibers. In our programs, Y and W are magnified by a factor of 100.

Our regularization parameters are spacing independent:

$$\Lambda(r_j) = \lambda_0 \exp(d\lambda |r_j - r_{center}|) \quad (7)$$

FIGS. 3(a) through 3(e) show images obtained for $X^{(1)}$ in Eq.(4) with different regularization parameters. Using large $\lambda_0$, the image of the hidden object has already appeared after the first iteration. With a decreasing of $\lambda_0$ down to $10^{-2}$, the image is gradually broken.

FIGS. 4(a) through 4(h) show the results of different numbers of iterations, when the small regularization $\lambda_0$ is used. We see that after m=50 iterations, the image of the hidden object begins to appear. After m=500, the image becomes stable as no visible change in the shape of the object occurs between m=500 to m=2000.

Figure 5A:
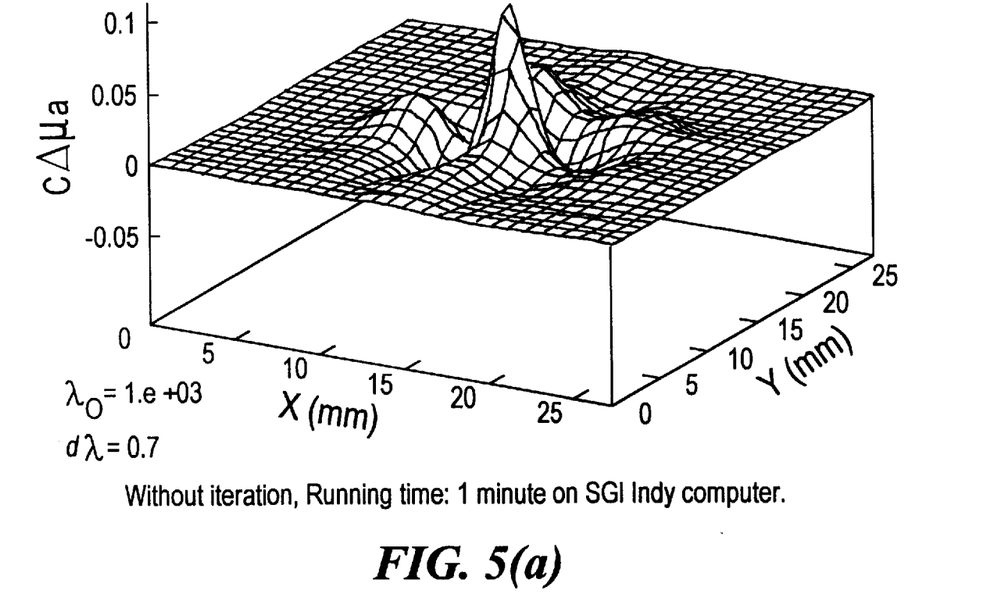
FIGS. 5(a) and 5(b) are comparative images of the object of FIG. 1(a) obtained using the method of the present invention with (a) a comparatively great degree of regularization and no iteration; and (b) a comparatively low degree of regularization and 2000 iterations, respectively.
Figure 5B:
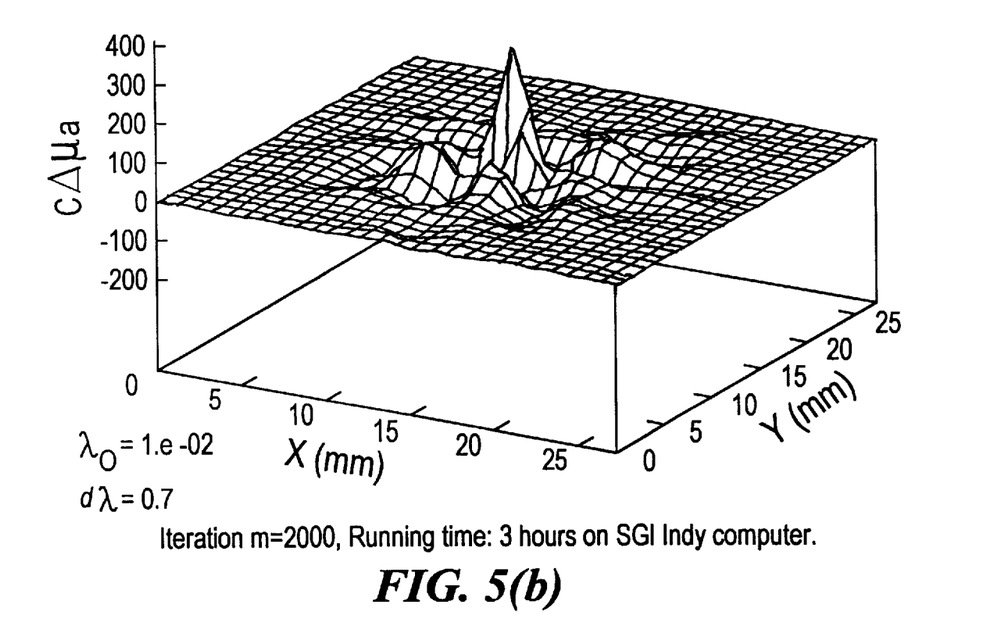

FIGS. 5(a) and 5(b) show an image obtained where (a) $\lambda_0=1000$, without iteration, by running 1 minute on a Silicon Graphic Incorp. (SGI) Indy computer where $[W^TW+\Lambda]^{-1}$ is stored; and (b) $\lambda_0=10^{-2}$, with 2000 iterations, by running 3 hours on the same computer, respectively. As can be seen, the two images are similar, but the latter has better resolution. Noting that the difference of regularization parameters for these two images is up to 5 orders of magnitude, the stability of the imaging process for the present technique is confirmed.

In both FIGS. 5(a) and 5(b), the presence of an absorber can be clearly seen. The location of the maximum change is about 7 mm away from the center which is about the actual location of the object (10 mm). The full width of half maximum of the absorber is 8 mm which is comparable to the diameter of the object (4.8 mm). The fluctuation at other spatial locations are less than one third of the peak value. Using different regularization parameters, the same location of the absorber was found, but the maximum peak value and the full width of half maximum were different. One possible reason that the center of the image deviates from that of the experimental set is that the hidden object is not a pure transparent scattering absorber, and the possible effect of reflection on the surface of the rod was not included in our physical model.

Figure 6:
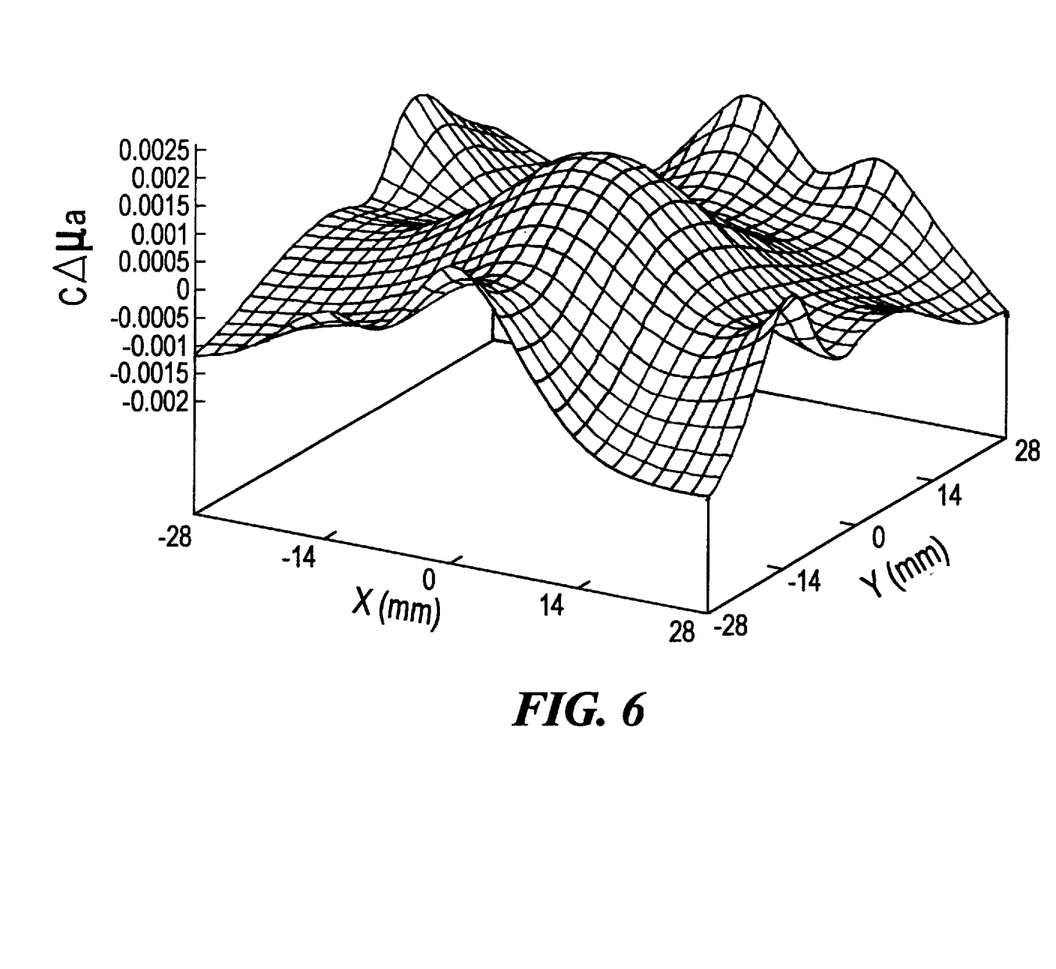
FIG. 6 is an image of the object of FIG. 1(a) obtained using the conventional Simultaneous Algebraic Reconstruction Technique (SART) after 3 hours and 100 iterations.

For comparison, the result using the SART inversion algorithm, commonly used by others, after 100 iterations (taking X=0 as initial input), which runs 3 hours on the same SGI workstation, is shown in FIG. 6. There is no clear image of the absorber, noticing that the maximum absorption coefficient is only 0.0025 which is about 40 times smaller than that obtained by our new algorithm.

We have also tested our technique on simulated temporal data with 30% white noise added. A clear image of a single absorber on the correct position was obtained. These results show that our approach is noise-resistant. This inversion method can include a change of diffusion coefficients, $\Delta D(\vec{r})$ or $\Delta \mu_s(\vec{r})$, as described before for detecting scattering defects in a highly scattering host medium.

The following comments, observations, objects, features, uses, applications and/or advantages may be made about the present invention:

(1) Intensity temporal profiles at multiple time windows/slices of scattered light pulses around turbid media are measured using multiple source detector pairs and are used as input data for the inversion to obtain the image maps of the media.

(2) An image reconstruction algorithm for imaging highly scattering turbid media is developed. The inversion procedure consists of input scattered light intensity data at different time slices, physical modeling of light propagation in random media, inversion computation algorithm, reconstructed image of spatial distributions of key optical parameters of random media, and image displays.

(3) Using different theoretical models for describing photon migration in random media for imaging. The theory includes transport theory for photon migration, and its approximations, such as the diffusion theory and the telegraph equations.

(4) Key optical parameters, such as the absorption coefficient, the index of refraction, the transport scattering length, the scattering length, and the diffusion constant, are mapped for imaging the internal structure of the turbid media at different light wavelengths. A difference in both absorption and scattering can be imaged to form a map of the internal structure of the turbid media in 3-D.

(5) A fast inversion algorithm is developed based on Shaw's principle, Eq. (4), in which the weight function matrix, W (Eq.(3)), which relates a change in the properties of turbid media to the changes in measured light intensities, can be pre-computed and stored for fast image inversion for each patient.

(6) A cumulant formula is developed to relate the experimentally measured intensities to the prediction from theoretical models based on properties of the turbid media.

(7) 3-D images of spatial distribution of key optical parameters of turbid media can be obtained using this algorithm. 2-D slices of tomographic images can be obtained by taking a section of a 3-D image and displaying it to highlight the location of tumors.

(8) Use the algorithm to image non-invasively tumors and abnormality in human body, such as tumor growths in breasts, tumors in brain, cerebral hemorrhage in brain, hemorrhage in internal organs, prostate.

(9) Using the algorithm with temporal data at various NIR wavelengths from 700 to 1500 nm for image reconstruction for monitoring metabolic states of a given part of human body.

(10) This novel inverse reconstruction method can be combined with shadowgram type of image techniques to further improve spatial resolution and enhance the presence of the abnormality.

(11) Use single source optical fiber and multiple detector fibers for collecting temporal profiles of the scattered pulses.

(12) Use multiple input source fibers and multiple detector fibers for collecting temporal profiles of the scattered pulses. A time sharing beam deflector will be incorporated to switch the input from one source fiber to another.

(13) Multiple S-D optical fibers are mounted on bra-like or hat-like holders surrounding a breast or a head (brain) to detect temporal intensity profiles of scattered pulses from breast or head (brain) for imaging the internal structure of optical properties.

(14) The lasers used for imaging are $Cr^{4+}$ Forsterite, $Cr^{4+}$ YAG, semiconductor lasers, Nd:YAG, and/or Ti:Sapphire lasers. The laser pulses at different wavelengths will be coupled to optical fiber by a time sharing scheme to deliver to the scattering media for spectral imaging.

(15) Temporal intensity profiles of scattered pulses around scattering media are measured using time resolved detection methods, including streak camera, ultrafast pin diodes, fast photomultipliers.

(16) Reconstructed images are to be displayed in 3-D or in 2-D tomography slices.

(17) Manipulating images obtained from claim 9 at different wavelengths to construct difference, sum, ratio and/or sum of ratio image maps at two wavelengths or several wavelengths to highlight tumors and to differentiate benign from malignant tumors.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of imaging an object located in a highly scattering turbid medium, said method comprising the steps of:

(a) illuminating the object through the highly scattering turbid medium with a pulse of light, whereby the light emergent from the highly scattering turbid medium consists of a ballistic component, a snake-like component and a diffusive component;
(b) determining the intensity of said diffusive component at a plurality of points in time; and
(c) using said intensity determinations to form an image of the object in the highly scattering turbid medium, said using step comprising using a mathematical inversion algorithm to generate an image of the highly scattering turbid medium, said mathematical inversion algorithm being $$X^{(K+1)^T} = [Y^T W + X^{(K)^T} \Lambda][W^T W + \Lambda]^{-1}$$

wherein W is a matrix relating output at detector position $r_d$, at time t, to source at position $r_s$, $\Lambda$ is a regularization matrix, chosen for convenience to be diagonal, but selected in a way related to the ratio of the noise, <nn> to fluctuations in the absorption (or diffusion) $X_j$ that we are trying to determine:

$$\Lambda_{ij} = \lambda_j \delta_{ij} \text{ with } \lambda_j = <nn>/<\Delta X_j \Delta X_j>$$

Here Y is the data collected at the detector, and $X^k$ is the kth iterate toward the desired absorption information.

2. The method as claimed in claim 1 wherein said pulse of light has a wavelength in the visible to near infrared region of the spectrum.

3. The method as claimed in claim 2 wherein said pulse of light has a wavelength of about 700 nm to about 1500 nm.

4. The method as claimed in claim 1 wherein said pulse of light is an ultrashort pulse of light.

5. The method as claimed in claim 1 wherein said pulse of light is a laser pulse emitted from a laser selected from the group consisting of Ti:Sapphire lasers, $Cr^{4+}$ Forsterite lasers, $Cr^{4+}$ YAG lasers, semiconductor lasers and Nd:YAG lasers.

6. The method as claimed in claim 1 wherein said highly scattering turbid medium is a biological tissue.

7. The method as claimed in claim 6 wherein said biological tissue is selected from the group consisting of human breast tissue, human brain tissue, human neck tissue and human prostate tissue and wherein said object is a tumor.

8. The method as claimed in claim 6 further comprising the step of detecting cancerous tumors in said biological tissue using fluorescence spectroscopy.

9. The method as claimed in claim 1 wherein said determining step comprises measuring the intensity of light at a plurality of points in the time frame spanning from 50 ps to 10 ns after illumination.

10. The method as claimed in claim 9 wherein said determining step comprises measuring the intensity of light at hundreds of points in the time frame spanning from 50 ps to 10 ns after illumination.

11. The method as claimed in claim 10 wherein said hundreds of points are determined by slicing the time frame into equal portions.

12. A method of forming a map of a highly scattering turbid medium, said method comprising the steps of:
(a) illuminating the highly scattering turbid medium with a first pulse of light along a first axis of incidence, whereby the light emergent from the highly scattering turbid medium due to said first pulse of light consists of a ballistic component, a snake component and a diffusive component;
(b) determining, at a plurality of times, the intensity of said diffusive component of the first pulse of light emergent from the highly scattering turbid medium at a plurality of locations;
(c) illuminating the highly scattering turbid medium with a second pulse of light along a second axis of incidence, said second axis of incidence intersecting with said first axis of incidence, whereby the light emergent from the highly scattering turbid medium due to said second pulse of light consists of a ballistic component, a snake component and a diffusive component;
(d) determining, at a plurality of times, the intensity of said diffusive component of the second pulse of light emergent from the highly scattering turbid medium at a plurality of locations; and
(e) using the intensity determinations from steps (b) and (d) to generate a map of the highly scattering turbid medium, said using step comprising using a mathematical inversion algorithm to generate a map of the highly scattering turbid medium, said mathematical inversion algorithm being $$X^{(K+1)^T} = [Y^T W + X^{(K)^T} \Lambda][W^T W + \Lambda]^{-1}$$

wherein W is a matrix relating output at detector position $r_d$, at time t, to source at position $r_s$, $\Lambda$ is a regularization matrix, chosen for convenience to be diagonal, but selected in a way related to the ratio of the noise, <nn> to fluctuations in the absorption (or diffusion) $X_j$ that we are trying to determine:

$$\Lambda_{ij} = \lambda_j \delta_{ij} \text{ with } \lambda_j = <nn>/<\Delta X_j \Delta X_j>$$

Here Y is the data collected at the detectors, and $X^k$ is the kth iterate toward the desired absorption information.

13. The method as claimed in claim 12 wherein each of said first and said second pulses of light has a wavelength in the visible to near infrared region of the spectrum.

14. The method as claimed in claim 12 wherein each of said first and said second pulses of light has a wavelength of about 700 nm to about 1500 nm.

15. The method as claimed in claim 12 wherein each of said first and said second pulses of light is an ultrashort pulse of light.

16. The method as claimed in claim 12 wherein each of said first and said second pulses of light is a laser pulse emitted from a laser selected from the group consisting of Ti:Sapphire lasers, $Cr^{4+}$ Forsterite lasers, $Cr^{4+}$ YAG lasers, semiconductor lasers and Nd:YAG lasers.

17. The method as claimed in claim 12 wherein said highly scattering turbid medium is a biological tissue.

18. The method as claimed in claim 12 wherein said biological tissue is selected from the group consisting of human breast tissue, human brain tissue, human neck tissue and human prostate tissue and wherein said object is a tumor.

19. The method as claimed in claim 12 wherein said determining steps each comprise time-resolving light emergent from the highly scattering turbid medium.

20. The method as claimed in claim 12 further comprising the steps of:
(f) illuminating the highly scattering turbid medium with a third pulse of light along a third axis of incidence, said third axis of incidence intersecting a plane defined by said first and second axes of incidence, whereby the light emergent from the highly scattering turbid medium due to said third pulse consists of a ballistic component, a snake component and a diffusive component; and
(g) determining, at a plurality of times, the intensity of said diffusive component of the third pulse of light emergent from the highly scattering turbid medium at a plurality of locations;

(h) wherein said using step comprises using the intensity determinations from steps (b), (d) and (g) to generate a map of the highly scattering turbid medium.

21. The method as claimed in claim 17 further comprising the step of detecting cancerous tumors in said biological tissue using fluorescence spectroscopy.

22. The method as claimed in claim 12 wherein said determining step comprises measuring the intensity of light at a plurality of points in the time frame spanning from 50 ps to 10 ns after illumination.

23. The method as claimed in claim 12 wherein said determining step comprises measuring the intensity of light at hundreds of points in the time frame spanning from 50 ps to 10 ns after illumination.

24. The method as claimed in claim 23 wherein said hundreds of points are determined by slicing the time frame at regular intervals.

25. The method as claimed in claim 12 wherein said map is an absorption map.

26. The method as claimed in claim 12 wherein said map is a scattering map.

* * * * *